United States Patent
Goellner et al.

(10) Patent No.: US 9,079,007 B2
(45) Date of Patent: Jul. 14, 2015

(54) DEVICE WITH AT LEAST ONE HOLLOW ELEMENT FOR CONVEYING A FLUID WITH A CONNECTION ELEMENT

(75) Inventors: Manfred Goellner, Berlin (DE); Johannes Mueller, Berlin (DE)

(73) Assignee: Berlin Heart GmbH, Berlin (DE)

( * ) Notice: Subject to any disclaimer, the term of this patent is extended or adjusted under 35 U.S.C. 154(b) by 210 days.

(21) Appl. No.: 13/510,353

(22) PCT Filed: Nov. 17, 2010

(86) PCT No.: PCT/EP2010/007066
§ 371 (c)(1),
(2), (4) Date: Sep. 21, 2012

(87) PCT Pub. No.: WO2011/060957
PCT Pub. Date: May 26, 2011

(65) Prior Publication Data
US 2013/0012926 A1     Jan. 10, 2013

Related U.S. Application Data

(60) Provisional application No. 61/262,280, filed on Nov. 18, 2009.

(51) Int. Cl.
*A61M 25/16* (2006.01)
*A61M 39/10* (2006.01)
(Continued)

(52) U.S. Cl.
CPC ............. *A61M 39/1011* (2013.01); *F16L 33/28* (2013.01); *F16L 33/30* (2013.01); *A61M 2039/1033* (2013.01)

(58) Field of Classification Search
CPC . A61M 39/00; A61M 39/10; A61M 39/1011; A61M 39/1055; A61M 39/12; A61M 16/0463; A61M 16/08; A61M 16/0816; A61M 16/0875; A61M 25/0014; A61M 2039/1033; F16L 13/00; F16L 37/02; F16L 37/04; F16L 37/08; F16L 37/092; F16L 33/00; F16L 33/003; F16L 33/006; F16L 27/00; F16L 27/02; F16L 27/023; F16L 33/28; F16L 33/30; F16L 33/32
USPC ......... 604/533, 534, 535, 536, 538, 539, 283; 285/921
See application file for complete search history.

(56) References Cited

U.S. PATENT DOCUMENTS 2,693,971 A * 11/1954 Harrison ........................ 285/269
4,254,773 A * 3/1981 Waldbillig ..................... 604/534
(Continued)

FOREIGN PATENT DOCUMENTS

| CA | 2 376 118 A1 | 3/2001 | ................ A61F 2/06 |
| DE | 202 18 931 U1 | 2/2003 | ............ A61M 25/00 |

(Continued)

OTHER PUBLICATIONS

International Search Report and Written Opinion, dated Jan. 3, 2001, pp. 1-8, International Patent Application No. PCT/EP2010/007066, European Patent Office, Netherlands.

*Primary Examiner* — Bhisma Mehta
*Assistant Examiner* — Nicholas Meghri
(74) *Attorney, Agent, or Firm* — Brinks Gilson & Lione (57) ABSTRACT

In an apparatus having at least one first hollow element for conducting a fluid having a connection element, to enable and facilitate a simple and reliable connection to a second hollow element, a snap-in element of the connection element having a latching surface which contacts an abutment surface in a connection state with the second hollow element is made as a radially widenable snap-in ring.

16 Claims, 4 Drawing Sheets

(51) Int. Cl.
 *F16L 33/28* (2006.01)
 *F16L 33/30* (2006.01)

(56) References Cited

U.S. PATENT DOCUMENTS

| | | | |
|---|---|---|---|
| 4,747,621 A | 5/1988 | Gans et al. | |
| 5,312,138 A | 5/1994 | Patera et al. | |
| 5,549,583 A * | 8/1996 | Sanford et al. | 604/535 |
| 5,827,249 A * | 10/1998 | Jensen | 604/349 |
| 6,164,558 A * | 12/2000 | Holt | 239/124 |
| 7,303,553 B2 | 12/2007 | Ott | 604/533 |
| 7,708,769 B1 | 5/2010 | Manzo et al. | 623/1.1 |
| 2007/0055357 A1 | 3/2007 | Pokorney et al. | 623/1.26 |
| 2008/0065000 A1 * | 3/2008 | Bidinger et al. | 604/9 |

FOREIGN PATENT DOCUMENTS

| | | | | |
|---|---|---|---|---|
| DE | 10 2006 035 257 A1 | 1/2008 | | A61M 25/18 |
| EP | 1 496 301 A2 | 2/2005 | | F16L 37/04 |
| WO | WO 9840036 | * | 9/1998 | A61F 2/06 |
| WO | WO 2004/001272 A1 | 12/2003 | | F16L 37/084 |

* cited by examiner

DEVICE WITH AT LEAST ONE HOLLOW ELEMENT FOR CONVEYING A FLUID WITH A CONNECTION ELEMENT

CROSS-REFERENCE TO RELATED APPLICATIONS

This application is a 371 nationalization of PCT/EP2010/007066, which in turn claims benefit of U.S. Provisional Application 61/262,280 filed Nov. 18, 2009, and European application 09075510.9 filed Nov. 18, 2009.

BACKGROUND

The invention relates to an apparatus having a hollow element, for example a tube, a hose or similar components for directing a fluid, for example a gas or a liquid, and having a connection element for connecting the hollow element to at least one further hollow element.

There is often the problem in the art of connecting different tubes, hoses or other lines in which fluids are conducted to one another reliably and fixedly.

For this purpose, a plurality of more or less complex and/or expensive solutions are known which can be realized under specific environmental conditions. In this respect, special environmental conditions such as difficult accessibility of the connection point or also the small construction size of the connection to be established require special solutions. There can also be a special demand that, despite the leak tightness of the connection, it should still be movable, for example rotatable about its longitudinal axis.

Particularly demanding boundary conditions are encountered in the field of medical engineering when, for example, such hollow elements are present in the form of hoses or cannulae in which body fluids, biocompatible liquids or other liquids have to be transported within a body. Such connections are, for example, difficult to access during surgical procedures and must, on the one hand, be able to be established with a reliable seal in a short time and, on the other hand, be able to be adapted to individual body dimensions in a space saving manner.

It is already known to establish such connection as crimp connections with a radial seal, as is addressed, for example, in the German utility model DE 202 18 931 U1 in a cannula adapter for soft catheters.

A plug-in catheter connection is, for example, known from the German laying-open document DE 10 2006 035 257 A1.

Finally, connection pieces are also known for the connection of hollow elements to blood vessels such as the T-shaped connection piece known from the Canadian patent CA 2376118 A1 which can be introduced into a blood vessel.

Finally, a connection apparatus is known from WO 2004/001272 A1 for cannulae having a coupler which allows a latch connection between the cannulae to be connected.

Against the background of the prior art, it is the underlying object of the present invention to realize an apparatus of the initially named kind in a particularly simple construction and in this respect to achieve a particularly simple handling.

SUMMARY

For this purpose, a connection element is provided at the first hollow element which is intended to be connectable or connected to a second hollow element for the directing of a fluid, said connection element having a deformable snap-in element having a latching surface which is configured so that it contacts an abutment surface connected to the second hollow element in a connection state of the two hollow elements. The snap-in element is made in accordance with the invention as a radially widenable snap-in ring. The latching surface can accordingly have a completely continuous annular surface or an annular surface interrupted in sector-like manner.

Such a snap-in ring has the advantage with respect to individual snap-in elements, for example in the form of snap-in hooks with latching noses, of being able to be manufactured more easily, for example in an injection molding process, wherein individual latching hooks may break or tear off, which can in particular have negative consequences on the use in surgical technology within a patient's body. A snap-in ring can moreover ensure a more secure connection since the abutment surfaces are larger and higher latching forces, i.e. inwardly directed holding forces of the snap-in ring, can be ensured in a simple manner, said holding forces acting against the widening of the snap-in ring and thus securing the established connection.

In addition, the snap-in connection is simply rotatable with a snap-in ring about the longitudinal axis without the catching of individual latching noses by their bending or by the catching at irregularities at, the counter-piece having to be feared. The corresponding latch connection can nevertheless be made releasable.

To establish the snap-in connection, a run-in chamfer can be provided at the snap-in ring in the form of a cone which effects the widening of the snap-in ring before the snapping in at the abutment surface on the pushing onto a counter-surface.

The snap-in ring can advantageously be elastically widenable by the material elasticity alone. For this purpose, it can be manufactured from an elastomer such as a silicone elastomer. The total connection element and optionally also the first and/or the second hollow element can comprise this material. A simple deformability of the addressed elements is thus also particularly easily possible for the purpose of the adaptation to the anatomical circumstances during an operation.

Provision can, however, also be made that one of the hollow elements is made as a rigid tube and the other hollow element is made as a flexible cannula.

The snap-in ring can generally also have radial slits in its longitudinal direction, in addition to its material-caused elasticity, said longitudinal direction extending parallel to its axis of symmetry and said radial slits facilitating the radial widening.

It is, however, generally also advantageous to manufacture the snap-in ring without slits to achieve smooth contours, a cylinder symmetry and thus a good rotatability about the longitudinal axis.

The handling of the apparatus in accordance with the invention becomes particularly simple in that at least the snap-in ring can be beaded radially outwardly over other parts of the connection element. The connection element with the widened snap-in ring can thus be brought into a suitable position with respect to the second hollow element and the overbeading can be reversed by stretching the connection element to lay the snap-in ring against the abutment surface of the second hollow element.

This is in particular advantageous when the snap-in ring is stabilized in the beaded over position. In this case, the snap-in ring can already be beaded over for the preparation of the operation or of the connection procedure, e.g. outside the patient's body in order then to be able to establish a corresponding connection efficiently by snapping in of the snap-in ring with a low effort during the operation. For this purpose, for example, only slight pushing against the snap-in ring is necessary to achieve the folding back of the snap-in ring and the reversing of the beading over.

To achieve the stabilization of the snap-in ring in the beaded over position in a simple manner, provision can be made in accordance with the invention that the connection element has a decrease in strength of the wall in an axially limited region. This can be realized in that cut-outs are provided in the corresponding axially bounded region in the connection element at its periphery or cut-outs are provided in the wall of the connection element which weaken the cross-section. In the simplest case, an inwardly or outwardly peripheral groove can be provided at the connection element. The connection element can alternatively or additionally also comprise a less stiff material in the axial section than in the other regions.

Provision can advantageously be made in accordance with the invention that the connection element is made cylindrical and has a respective radially widenable snap-in ring at both ends which cooperates with a respective abutment surface at a respective hollow element. The connection element can thus be connected both to the first hollow element and to a second hollow element by snapping in in each case of a snap-in ring at an abutment surface. An improved rotatability of the total arrangement about the longitudinal axis thus results and more possibilities for handling result since the connection element can selectively first snap onto the first or second hollow element and can then be snapped onto the respective other hollow element during an operation.

Alternatively to this, the connection element can also be connected in one piece to the first or second hollow element or can be connected thereto by adhesive bonding or welding. This can facilitate the handling to the extent that all the parts required for the establishing of a connection are absolutely available at a connection point without additional measures. In this case, one snap-in connection fewer has to be established since it is replaced in manufacture by a fixed connection so that the total effort in establishing a connection on site is reduced. The connection piece can, for example, be manufactured in one piece in an injection molded process together with the first hollow element.

The invention moreover relates to an apparatus of the above-described kind in which the first or second hollow element is made as a blood vessel connection piece having a radially outwardly projecting connection flange at its end opposite the snap-in element. A simple and reliable connection between a cannula and a blood vessel is, for example, intended to be able to be established by such a blood vessel connection piece. It is usual to sew on a cannula head (graft) to a vessel for this purpose. Such connections have not previously worked ideally since the geometry of the corresponding components is not or cannot be adapted ideally to the anatomical circumstances. The present invention should in this connection allow subsequent position corrections particularly simply and permit an adaptation to the anatomical circumstances which is as good as possible by preselection of the geometrical parameters. In addition, such a blood vessel connection piece should be connectable to further hollow elements in a simple manner without even larger forces acting on the blood vessel connection piece or without it having to be moved to a substantial degree after the connection to a blood vessel.

Provision is made in accordance with the invention for an optimized sealing at a blood vessel that the connection flange has a convex sealing surface. This sealing surface can in the simplest case form a surface section of the surface of a hollow cylinder in that it extends in a straight manner in one direction, the longitudinal direction of the blood vessel, and in a circular manner in cross-section in a second direction. The connection surface can, however, also have a non-circular, round cross-section in the second direction, for example an elliptic or otherwise rounded cross-section which corresponds to the correspondingly anatomically present real cross-sections of blood vessels.

The blood vessel connection piece can advantageously have a conical sealing surface at its end opposite the connection flange. A counter-piece of a further hollow element which is to be connected to the blood vessel connection piece can be in contact with said sealing surface. In this respect, the sealing surface of the blood vessel connection piece can have a conical inner contour or a conical outer contour, with the counter-surface of the further hollow element in each case having a correspondingly shaped counter-surface.

Provision can also advantageously be made that the blood vessel connection piece has a spherical guide surface and/or sealing surface at its end opposite the connection flange. For this purpose, the blood vessel connection piece can, for example, have a hollow spherical inner surface at its end into which a part of an outer surface of a sphere of a counter-piece of a further hollow element is inserted or the blood vessel connection piece can have an outer surface of a part sphere which sealingly projects into a corresponding part surface of a hollow sphere of a counter-piece.

A pivotability and rotatability of the blood vessel connection piece to all sides with respect to a hollow element to be connected thereto is ensured by this construction.

If the pivotability remains within tight angular limits, the connection can be reliably secured and can be established particularly simply by a connection piece of the above-described kind having one or more snap-in rings at its ends. In this respect, it can prove to be particularly advantageous if the connection piece is elastic overall so that it is flexible on the pivoting toward one another of the two hollow elements to be connected without the respective snap-in ring being substantially deformed.

The apparatus in accordance with the invention allows a simple and reliable establishing of a connection between a plurality of hollow elements, in particular medical cannulae, with the manufacturing effort remaining small due to the simple construction realization. The use of a blood vessel connection piece of the described kind per se without a connection piece having a snap-in ring can also be advantageous per se and can achieve specific technical objects. In this respect, in such a connection piece, either a spherical sealing surface combination as described above can be used or a flexibility of the connection piece can be realized by corresponding material selection or by a use of a corrugated hose at least over apart of the length of the connection piece. It can also be contemplated to have a plurality of corresponding connections pieces with different preset offsets available.

BRIEF DESCRIPTION OF THE DRAWINGS

The invention will be shown and subsequently described in the following with reference to an embodiment in a drawing.

There are shown in

DESCRIPTION OF PREFERRED EMBODIMENTS

Figure 1:
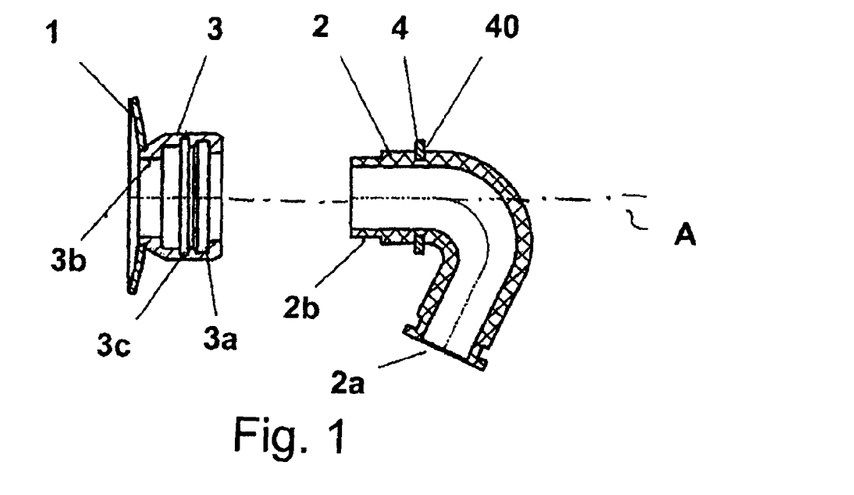
FIG. 1 in a longitudinal section, a first and a second hollow element as well as a connection element connected to the first hollow element.

FIG. 1 shows, in the left hand part, as an example for a hollow element which is flowed through by a fluid, a so-called suture ring 1 which can, for example, be sewed to a heart and which is connected to one end 2b of an inlet cannula 2 at whose other end 2a a blood pump can be arranged.

A further cannula for other purposes can, however, also be provided instead of the suture ring 1.

Figure 2:
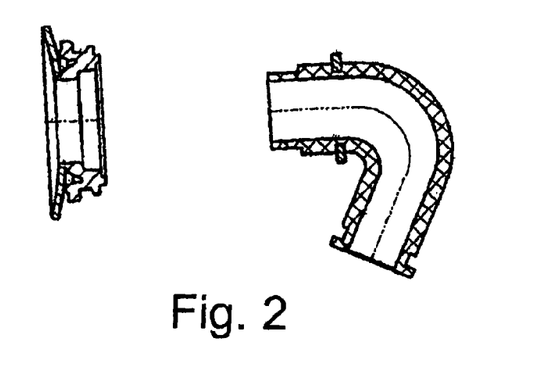
FIG. 2 the arrangement of FIG. 1 with a beaded over connection element.

The suture ring 1 bears an elastic coupler 3 which is made of silicone, which represents the connection element and which is adhesively bonded to the suture ring 1. The suture ring 1 can be connected to the cannula 2 by means of the connection piece 3. For this purpose, as shown in FIG. 2, the coupler 3 is first outwardly beaded over in the region of the inner groove 3c. In this position, the connection element is independently stabilized by the elastic widening of its end having the abutment surface 3a and its corresponding endeavor to compress radially. In this position, the suture ring with the coupler prepared in this manner can be handled easily during the operation.

The end 2b of the cannula 2 is inserted into the coupler 3, with the narrowest region 3b of the coupler advantageously having a smaller diameter than the end 2b of the cannula so that a sealing is achieved here by elastic pressure in the radial direction. After the insertion of the cannula 2 into the coupler 3, the beaded over part of the coupler 3 is again stretched so that the abutment surface 3a of the coupler 3 cooperates with the abutment surface 4a of the rigid ring 4 inserted into the cannula 2. The suture ring 1 and the cannula 2 are thus also held together in the axial direction (axis A). In addition the contact between the abutment surfaces 3a, 4a can also effect a sealing in the axial direction.

The ring 4 can be adhesively bonded into a groove of the cannula 2 or elastically snapped into it. The ring 4 can for this purpose be made as a rigid ring, for example, made of metal, in a slit form or also as an elastic, continuous ring.

Figure 3:
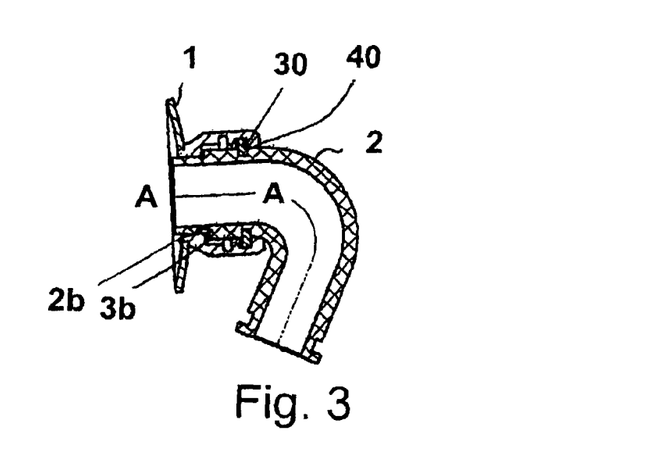
FIG. 3 the arrangement of FIG. 1, with the hollow elements being connected to one another.

The joined together position of the suture ring 1 and of the cannula 2 is shown in FIG. 3. It can also be recognized there that the region 2b of the cannula fits together in form-fitted manner with the region 3b of the coupler 3.

The abutment surface 3a of the coupler is equally pressed toward the abutment surface 4a of the ring 4 in the axial direction.

It must be noted that the coupler element 3 could also be connected in one piece to the suture ring 1 or that the suture ring 1 could have a stub with a ring similar to the ring 4 with which the coupler can cooperate in the same manner as with the cannula 2 on the oppositely disposed side.

The inner groove 3c in the coupler is designed such that the remaining wall thickness is considerably weakened, as can be recognized on the left hand side in FIG. 1, so that the coupler 3 can be outwardly turned over/beaded over most easily at this point. The weakening is configured as an inwardly or outwardly facing peripheral groove in the wall of the connection piece, wherein the groove of the connection piece is configured for beading over the snap-in ring at the groove, wherein a wall thickness of the connection piece at the groove is less than a wall thickness of the snap-in ring. It is helpful in this respect if the part of the coupler 3 to be beaded over has a smaller inner diameter at least at points than the outer diameter of the coupler in the region of the inner groove 3c so that the coupler stabilizes itself particularly well in the beaded over state.

The ring 4 which forms the abutment surface 4a in the region of the cannula 2 for cooperation with the abutment surface 3a of the coupler can also be made in one piece with the cannula.

The dimensions of the coupler and the material of the ring 4 can also be designed so that at least one of these elements is elastically deformable and such that, in the joined together state of the two hollow elements, an axial pull bears on the coupler 3 so that an axial seal is present in the region of the abutment surfaces 3a, 4a. This can be present in addition to or alternatively to the described radial sealing of the joined together regions 2b, 3b.

Figure 4:
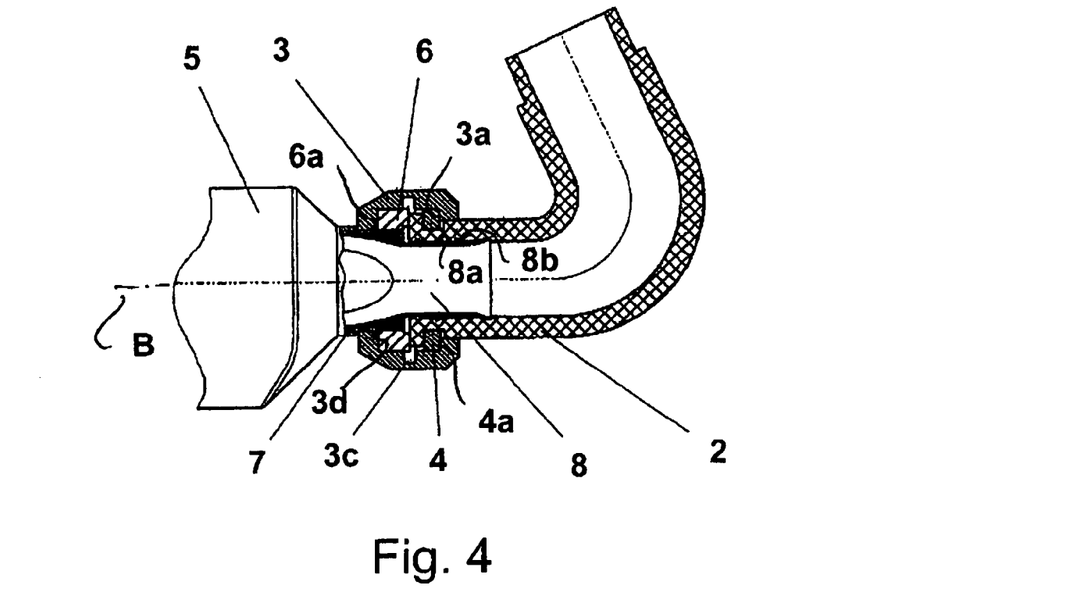
FIG. 4 in a longitudinal section, a connection between a pump tube and a cannula.

FIG. 4 shows, in a longitudinal section, the connection of a cannula 2 to the pump tube 7 of a blood pump 5. The cannula 2 has, as described in FIGS. 1-3, an inserted ring 4 which has an abutment surface 4a which cooperates with a corresponding abutment surface 3a of a coupler 3. The coupler 3 is placed over a ring 6 in the case of FIG. 4, said ring being fixedly connected, for example welded or adhesively bonded, to the pump tube 7 and having an abutment surface 6a which cooperates with an abutment surface 3d of the coupler 3. The coupler can be beaded over the inner groove 3c in this sense both toward the side of the cannula 2 in order then to be connected to the pump tube in a simple manner and also conversely, the coupler 3 can be beaded over toward the side of the pump tube 7 in order then to be able to be connected simply to the cannula.

Provision can, however, also be made that the coupler 3 is fixedly connected, for example adhesively bonded, to the ring 6 and/or to the pump tube 7 in the region of the abutment surface 3d. The pump tube 7 has a so-called olive 8 which is made as a tube stub having outwardly facing, so-called knife-edged rings. These knife-edged rings are made in the form of saw teeth in longitudinal section and running in ring form around the olive so that they can be embedded into the elastic material of the cannula 2 as rings and can thus form a radial sealing.

Two knife-edged rings are labeled by 8a, 8b in FIG. 4. Despite the elastic and partly shape-matched connection between the cannula 2 and the pump tube or the olive 8, the arrangement is rotatable about the axis B in order to be able to adapt the construction to anatomical circumstances on the joining together of the parts.

Figure 5:
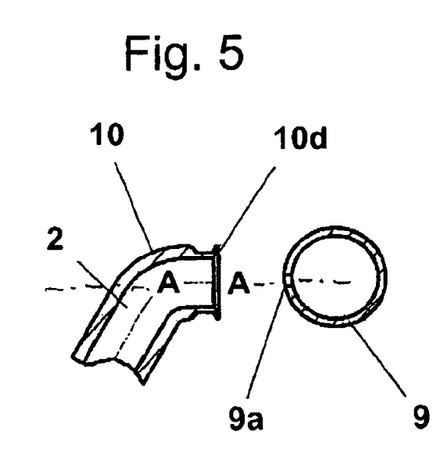
FIG. 5 in a longitudinal section, the end of a cannula and, in cross-section, a blood vessel.

FIG. 5 schematically shows in a longitudinal section a cannula 2 in accordance with the prior art which is intended to be connected via a cannula head 10 to a blood vessel 9 shown in cross-section. For this purpose, an end face 10d of the cannula head 10 is provided which is designed to be adapted as easily as possible to the outer shape of the blood vessel 9.

Figure 6:
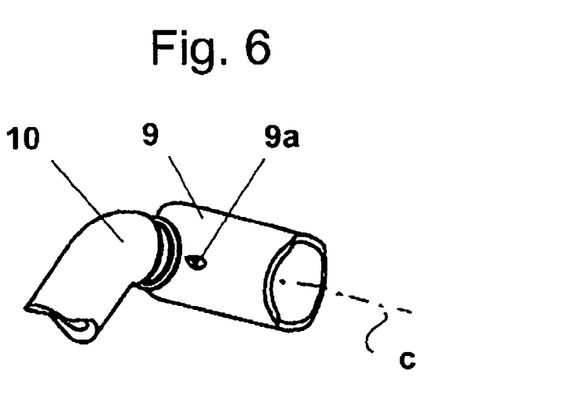
FIG. 6 in a three dimensional representation, the end of a cannula with a blood vessel connection piece and a blood vessel.

FIG. 6 shows the corresponding arrangement known per se in a three-dimensional representation, with an opening 9a intended to be made in the blood vessel 9 which can be introduced by a surgeon in the shape of a longitudinal incision along the longitudinal axis C of the blood vessel 9. The corresponding connection between the cannula head 10 and the blood vessel 9 is designed by the invention to be configured so that an elastically sealing contact surface is present which can be provided by a corresponding shape of the end surface 10d and which can, for example, be made three-dimensionally partly cylindrical or similar.

In addition, the cannula 2 should be rotatable about the axis A with respect to the blood vessel to be able to configure the arrangement individually.

Figure 7:
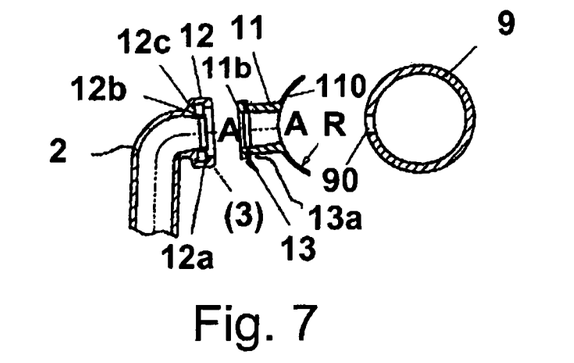
FIG. 7 in a section, a cannula, a blood vessel connection piece and a blood vessel.

At least the cannula 2 should be able to be connected to the blood vessel fast and simply and should be able to be separated from it again as required. For this purpose, the above-described connection method in accordance with the invention with the aid of a connection piece which can be beaded over presents itself which will be explained more precisely in the following with reference to FIGS. 7ff.

FIG. 7 for this purpose shows a blood vessel connection piece 11 which has a connection flange 11a. The connection flange 11a is shown part cylindrical, for example, so that it is prepared for connection to a blood vessel 9 circular in cross-section. Other cross-sections of the connection flange 11a are likewise conceivable. They can be made, for example, partly elliptical and their curvature or diameter R can comply with the size of the blood vessel 9.

The blood vessel connection piece 11 bears at its end facing the cannula 2 a rigid ring 13 which is tightly connected to the blood vessel connection piece, for example manufactured in one piece with it or welded or adhesively bonded to it and bears an abutment surface 13a.

Figure 9:
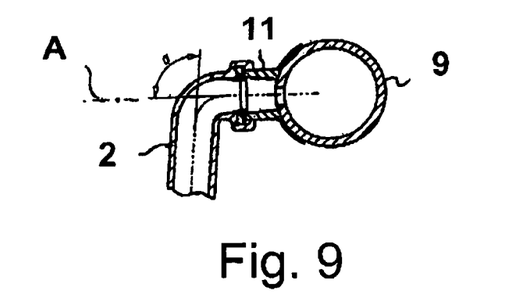
FIG. 9 the arrangement of FIG. 7 in the connected state.

At the end of the cannula 2, the connection piece 3 is connected to it in one piece. Said connection piece has an abutment surface 12a which cooperates in the connected state with the corresponding abutment surface 13a of the ring 13, as shown in FIG. 9.

The corresponding brim groove is labeled by 12c and weakens the connection piece 3 at its inner side such that the overbeading is simple and self-stabilizing to the rear toward the cannula 2.

A conical attachment at the cannula 2 is labeled by 12b and converges toward the end of the cannula 2 and cooperates in the connected state with a corresponding hollow cone 11b at the blood vessel connection piece 11 so that on this connection a tilting of the longitudinal axes of the two hollow elements toward one another by a specific amount is possible without losing the sealing effect of the conical sealing elements in this process. In addition, the connection is rotatable without problem about the axis A without the seal tightness being impaired.

To establish a connection between the cannula and the blood vessel 9, the suture ring/the blood vessel connection piece 11 is first sutured to the blood vessel 9 while using the connection flange 11a and thus a seal is established between the blood vessel connection piece and the vessel. The blood can now enter or exit through the opening 9a and pass through the blood vessel connection piece 11. The cannula 2 is sealingly connected to said blood vessel connection piece so that a blood pump can be connected to the blood vessel 9 via the cannula.

Figure 8:
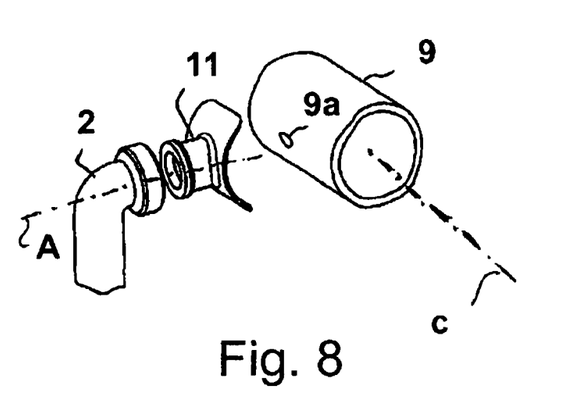
FIG. 8 the arrangement of FIG. 7 in a three-dimensional representation.

FIG. 8 shows the arrangement schematically in a three-dimensional view and FIG. 9 in a section in the joined together state.

In FIG. 9, the offset angle α of the cannula can be recognized which either can be preselected by selection of a suitable cannula or the cannula can be made flexible, for example wholly or sectionally as a corrugated hose to be able to achieve a corresponding offset.

Figure 10:
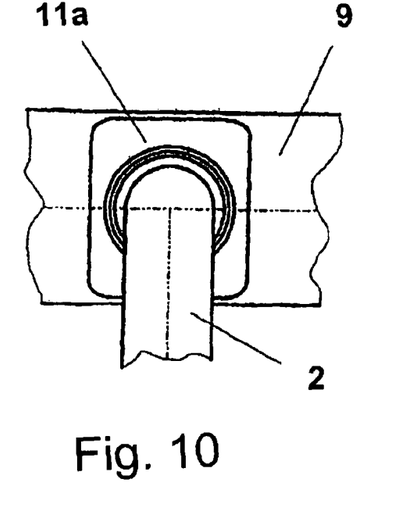
FIG. 10 a view of a blood vessel connection piece which is set onto a blood vessel.

FIG. 10 shows in a plan view in the direction of the axis A the cannula 2 connected to the blood vessel connection piece 11 before the blood vessel 9 to which the flange 11a of the blood vessel connection piece 11 is sutured.

Figure 11:
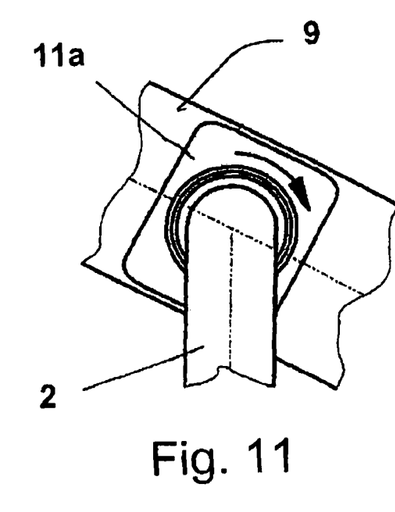
FIG. 11 the arrangement of FIG. 10, with the blood vessel connection piece being rotated with respect to the position shown in FIG. 10.

In comparison with this, FIG. 11 shows a similar view in which the blood vessel is rotated together with the blood vessel connection piece 11 about the axis A by a little with respect to the cannula 2. Such a rotation can be realized without problem and without any greater exertion of force thanks to the construction in accordance with the invention so that a tearing off of the suturing of the connection flange 11a to the vessel 9 is not to be feared.

Figure 12:
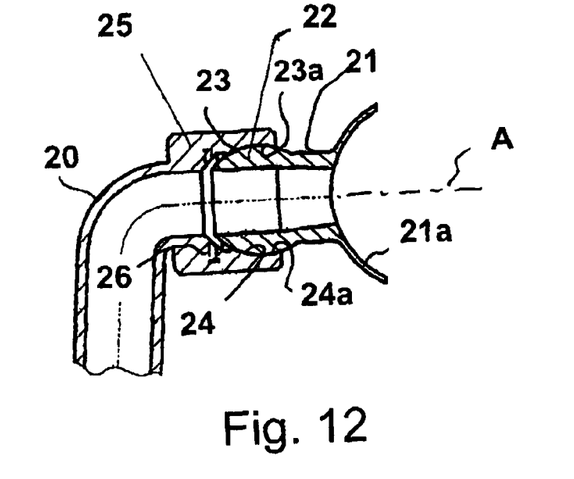
FIG. 12 an arrangement of a cannula end which is connected to a blood vessel connection piece by means of a connection element, in cross-section, with a ball joint being provided between the blood vessel connection piece and the cannula end.

Both the cannula 2 and the blood vessel connection piece with the connection flange 11a can comprise, for example, a silicone elastomer to achieve the corresponding movability. Finally, FIG. 12 shows in a longitudinal section the connection between a cannula 20 and a blood vessel connection piece 21 with a connection flange 21a. The blood vessel connection piece 21 has a spherical end piece 22 with a partly spherical sealing surface 23. The latter cooperates with a hollow spherical sealing surface 24 which is arranged at a coupler 25 which is connected in one piece to the cannula 20. The coupler 25 is made as a connection piece whose hollow spherical sealing surface 24 is formed as an abutment surface in the region 24a which engages behind the spherical end piece 22 of the blood vessel connection piece. This abutment surface 24a cooperates with the corresponding region 23a of the hollow spherical sealing surface of the connection piece 25 such that the cannula 20, on the one hand, and the blood vessel connection piece 21, on the other hand, can be axially held together along the axis A in FIG. 12. The connection piece 25 can, equally as shown in the previously described Figures, also be outwardly beaded over toward the cannula 20 to be able to establish the connection during an operation simply by a snapping back of the coupler. For this purpose, an inner groove can be provided at the connection piece 25 in the region which is show by broken lines and is labeled by 26. The connection piece 25, can, like the cannula 20, be elastic and can be made from a silicon elastomer.

The embodiment shown has the property that the cannula 20 and the blood vessel connection piece 21 are rotatable with respect to one another about the axis A, on the one hand, and are also, on the other hand, tiltable at least a little, for example by 5 to 10 degrees, with respect to one another with respect to this axis. The sealing between the spherical surfaces 23, 24 is not at risk in this process and the abutment surfaces 23a, 24a also remain functional.

The simple handling on the joining together of the hollow elements 20, 21 by means of the connection element 25 is in this respect equally present as in the examples shown in FIGS. 1-11.

It is meaningful to set the offset of the cannula 20 as much as possible to the required circumstances so that the tilting between the cannula 20 and the blood vessel connection piece 21 is minimized in actual use to minimize the throughflow resistance of this connection and thus also to minimize turbulence of the blood flowing therethrough to permanently avoid damage to or deposits of the blood.

The connection element 25 can also, in contrast to FIG. 12, be connected to the blood vessel connection piece 21 in a similar embodiment and can accordingly elastically engage around a spherical sealing surface of the cannula 20.

The embodiment of the connection in accordance with the invention between two hollow elements allows, equally as the embodiment in accordance with the invention of a blood vessel connection piece, a particularly simple handling of the corresponding parts during an operation, with a particularly low proneness to defects being associated with this together with a high reliability and seal tightness of the connection.

Aspects of the invention will be presented in the following:

An aspect of the invention relates to an apparatus having at least one first hollow element (1, 2, 11, 20) for conducting a fluid and having a connection element (3, 25) which has a deformable snap-in element having a latching surface (3a, 3d, 12a, 24a) which contacts an abutment surface (4a, 13a, 23a) connected to a second hollow element in a connection state, with the snap-in element being a radially widenable snap-in ring.

A further aspect of the invention relates to an apparatus in which the snap-in ring can be elastically widened by material elasticity.

A further aspect of the invention relates to an apparatus in which the snap-in ring is made peripherally non-slit.

A further aspect of the invention relates to an apparatus in which at least the snap-in ring can be radially outwardly beaded over other parts of the connection element (3, 25).

A further aspect of the invention relates to an apparatus in which the snap-in ring is stabilized in the beaded over position.

A further aspect of the invention relates to an apparatus in which the connection element (3, 25) has a weakening of the wall (3c) in an axially bounded region.

A further aspect of the invention relates to an apparatus in which the connection element (3, 25) is cylindrical and has at both ends a respective radially widenable snap-in ring which cooperates with a respective abutment surface (4a, 13a, 23a) at a respective hollow element (1, 12, 11, 20).

A further aspect of the invention relates to an apparatus in which the connection element (3, 25) is connected in one piece to the first hollow element (1, 2, 11, 20) or is connected thereto by adhesive bonding or welding.

A further aspect of the invention relates to an apparatus in which the first or second hollow element (11) is made as a blood vessel connection piece having a radially outwardly projecting connection flange (11a) at its end opposite the snap-in element.

A further aspect of the invention relates to an apparatus in which the connection flange (11a) has a convex connection surface.

A further aspect of the invention relates to an apparatus in which the connection surface extends in a straight manner in a first direction and has a round, in particular partly circular, cross-section in a second direction corresponding to the outer contour of a blood vessel (9).

A further aspect of the invention relates to an apparatus in which the blood vessel connection piece (11) has a conical sealing surface (11b) at its end opposite the connection flange (11a).

A further aspect of the invention relates to an apparatus in which the blood vessel connection piece (11) has a spherically surfaced sealing surface (23) at its end opposite the connection flange (11a).

The named aspects can advantageously be combined with one another in different configurations.

The invention claimed is:

1. An apparatus having at least one first hollow element for conducting a fluid and having a connection piece which has a deformable snap-in element having a latching surface which contacts an abutment surface connected to a second hollow element in a connection state, wherein the latching surface and the abutment surface are configured as sealing surfaces which permanently exert axial pressure against each other in the connection state to establish axial sealing, wherein the snap-in element is a radially widenable snap-in ring which can be radially outwardly beaded over other parts of the connection piece, wherein the connection piece has a weakening of a wall of the connection piece in an axially bounded region, wherein the weakening is configured as an inwardly or outwardly facing peripheral groove in the wall of the connection piece, wherein the groove of the connection piece is configured for beading over the snap-in ring at the groove, wherein a wall thickness of the connection piece at the groove is less than a wall thickness of the snap-in ring.

2. An apparatus in accordance with claim 1, wherein the snap-in ring can be elastically widened by material elasticity.

3. An apparatus in accordance with claim 1 or claim 2, wherein the snap-in ring is made peripherally non-slit.

4. An apparatus in accordance with claim 1, wherein the snap-in ring is stabilized in the beaded over position.

5. An apparatus in accordance with claim 1 or claim 2, wherein the snap-in ring, at least at one point of the snap-in ring, has an inner diameter smaller than the outer diameter of the connection piece at the groove to stabilize the snap-in ring in the beaded over position.

6. An apparatus in accordance with claim 1, wherein the connection piece is cylindrical and has at both ends a respective radially widenable snap-in ring which cooperates with a respective abutment surface at a respective hollow element.

7. An apparatus in accordance with claim 1 or claim 2, wherein the connection piece is formed in one piece with the first hollow element or is connected thereto by adhesive bonding or welding.

8. An apparatus in accordance with claim 1, wherein the first or second hollow element is made as a blood vessel connection piece having a radially outwardly projecting connection flange at its end opposite the snap-in element.

9. An apparatus in accordance with claim 8, wherein the connection flange has a convex connection surface.

10. An apparatus in accordance with claim 9, wherein the connection surface extends in a straight manner in a first direction and has a round, in particular partly circular, cross-section in a second direction corresponding to an outer contour of a blood vessel.

11. An apparatus in accordance with claim 8, claim 9, or claim 10, wherein the blood vessel connection piece has a conical sealing surface at its end opposite the connection flange.

12. An apparatus in accordance with claim 8, claim 9 or claim 10, wherein the blood vessel connection piece has a spherically surfaced sealing surface at its end opposite the connection flange, wherein the abutment surface is a portion of the spherical sealing surface, wherein the latching surface of the snap-in ring is a portion of a hollow spherical sealing surface, wherein the spherical sealing surface cooperates with the hollow spherical sealing surface in the connection state to allow for tilting a first longitudinal axis of the first hollow element relative to a second longitudinal axis of the second hollow element to vary a tilting angle between the first and second longitudinal axes.

13. An apparatus in accordance with claim 1, wherein the inner diameter of the snap-in ring is smaller than the inner diameter of the connection piece at the groove.

14. An apparatus in accordance with claim 1, wherein the wall thickness of the connection piece at the groove is less than a minimum wall thickness of the snap-in ring.

15. A method of connecting a first hollow element for conducting a fluid with a second hollow element, the first hollow element comprising a connection piece which has a deformable snap-in element, the snap-in element configured as a radially widenable snap-in ring having a latching surface to contact an abutment surface of the second hollow element in a connection state, wherein the connection piece has a weakening of a wall of the connection piece in an axially bounded region, wherein the weakening is configured as an inwardly or outwardly facing peripheral groove in the wall of the connection piece, and a wall thickness of the connection piece at the groove is less than a wall thickness of the snap-in ring, wherein the latching surface and the abutment surface are configured as sealing surfaces which permanently exert axial pressure against each other in the connection state to establish axial sealing, the method comprising the steps of: radially widening the snap-in element and beading the snap-in element radially outwardly over other parts of the connection piece at the groove of the connection piece, and stabilizing the snap-in ring in the beaded over position.

16. The method of claim 15, wherein the first or second hollow element is made as a blood vessel connection piece having a radially outwardly projecting connection flange at its end opposite the snap-in element, wherein the blood vessel connection piece has a spherically surfaced sealing surface at its end opposite the connection flange, wherein the abutment surface is a portion of the spherical sealing surface, wherein the latching surface of the snap-in ring is a portion of a hollow spherical sealing surface, wherein the spherical sealing surface cooperates with the hollow spherical sealing surface in the connection state to allow for pivoting tilting a first longitudinal axis of the first hollow element relative to a second longitudinal axis of the second hollow element to vary a tilting angle between the first and second longitudinal axes, the method further including the step of varying the tilting angle between the first and second longitudinal axis of the first and second hollow elements, by tilting the first longitudinal axis of the first hollow element relative to the second longitudinal axis of the second hollow element.

* * * * *

UNITED STATES PATENT AND TRADEMARK OFFICE
CERTIFICATE OF CORRECTION

PATENT NO. : 9,079,007 B2  
APPLICATION NO. : 13/510353  
DATED : July 14, 2015  
INVENTOR(S) : Manfred Goellner and Johannes Mueller

Page 1 of 1

It is certified that error appears in the above-identified patent and that said Letters Patent is hereby corrected as shown below:

On the Title Page

At item (30) Foreign Application Priority Data, insert --Nov. 18, 2009 (EPO) 09 07 5510.9--.

Signed and Sealed this  
Fifth Day of January, 2016

Michelle K. Lee  
*Director of the United States Patent and Trademark Office*